US006214343B1

(12) United States Patent
Kink et al.

(10) Patent No.: US 6,214,343 B1
(45) Date of Patent: Apr. 10, 2001

(54) PREVENTION AND TREATMENT OF NECROTIZING ENTEROCOLITIS

(75) Inventors: John A. Kink; Katherine L. Worledge, both of Madison, WI (US)

(73) Assignee: Ophidian Pharmaceuticals, Inc., Madison, WI (US)

( * ) Notice: Subject to any disclaimer, the term of this patent is extended or adjusted under 35 U.S.C. 154(b) by 0 days.

(21) Appl. No.: 09/318,109

(22) Filed: May 24, 1999

(51) Int. Cl.[7] .................. A61K 39/395; C07K 16/02; C07K 16/00
(52) U.S. Cl. .................. 424/158.1; 424/139.1; 424/141.1; 424/130.1; 514/2; 530/380; 530/388.23; 530/827; 530/389.1
(58) Field of Search .............. 424/139.1, 158.1, 424/141.1, 130.1; 514/2; 530/380, 388.23, 827, 389.1

(56) References Cited

U.S. PATENT DOCUMENTS 5,420,253 * 5/1995 Emery et al. .................. 530/423
5,747,532 * 5/1998 Lai .................................. 514/491
5,847,088 * 12/1998 Cousens et al. .............. 530/388.1

OTHER PUBLICATIONS

Muguruma et al. Prenat Neonat Med;3:571–579, 1998.*

* cited by examiner

Primary Examiner—Diana Dudash
Assistant Examiner—Shahnam Sharareh
(74) Attorney, Agent, or Firm—Medlen & Carroll, LLP

(57) ABSTRACT

Methods are described for preventing and treating necrotizing enterocolitis in animals, including humans. Antibodies directed to PAF and/or TNF are shown to have a beneficial effect in animal models predictive of human therapy for the treatment of necrotizing enterocolitis, which is a major life-threatening illness in neonates worldwide.

10 Claims, No Drawings

PREVENTION AND TREATMENT OF NECROTIZING ENTEROCOLITIS

FIELD OF THE INVENTION

The present invention relates to therapeutics for the prevention and treatment of necrotizing enterocolitis, and in particular the prevention and treatment of necrotizing enterocolitis in neonates through the use of antibody therapy.

BACKGROUND OF THE INVENTION

Necrotizing enterocolitis (NEC) has emerged as the most common gastrointestinal emergency in neonatal intensive care units (NICU). A. M. Kosloske, "Epidemiology of necrotizing enterocolitis," *Adcta Paediatr. Suppl.* 396:2 (1994). U. G. Stauffer, "Necrotizing enterocolitis," *Acta Paediatr* 83:666 (1994). NEC can occur endemically as isolated cases, or at times, epidemic clusters of cases are seen in neonatal nurseries. In the United States the incidence ranges from 1 to 3 per 1000 live births and roughly 1 to 7.7% of NICU admissions. R. C. Holman et al., "Necrotizing Enterocolitis Mortality in the United States, 1979–85" *AJPH* 79:8 (1989). The average annual mortality rate for NEC was 13.1 deaths per 100, 000 live births. In the United States, about 12,000 newborn infants per year develop NEC, with a mortality rate of up to 40%. Clinically, NEC is characterized by a triad of symptoms: abdominal distention and tenderness, gastrointestinal bleeding, and pneumatosis intestinalis, i.e., air within the intestinal wall. R. M. Kliegman and A. A. Fanaroff, "Necrotizing Enterocolitis" *New Eng. J. Med.* 310:1093 (1984). Death associated from NEC occurs from intestinal perforation with sepsis with shock, intravascular dissemination, pneumatosis, and short bowel syndrome resulting in malabsorption after resection.

The etiology and pathogenesis of NEC are unclear. Epidemiological studies point to (1) tissue injury or GI tract immaturity (2) infection, (3) oral feeding and (4) hypoxia. A. M. Kosloske, "A unifying hypothesis for pathogenesis and prevention of necrotizing enterocolitis" *J. Pediatrics* 117:S68 (1990). It is thought that an opportunistic member of the infants microbial flora in combination with tissue injury and/or gastrointestinal immaturity initiates the disease. The reduction in gut barrier function leads to the translocation of bacterial toxins, such as endotoxin, i.e., lipopolysaccride (LPS) or exotoxins. The increased local levels of these substances in the intestinal mucosa can then trigger a series of host responses and stimulate the production of proinflammatory phospholipids and/or cytokines such as platelet activating factor (PAF), tumor necrosis factor (TNF) and interleukins 1 and 6 (IL-1 and IL-6). W. Hsueh et al., "Interaction of Inflammatory Cytokines, Bacterial Products, and Lipid Mediators in Intestinal Injury" In: *Cytokines in Health and Disease* (2d Edition, eds. Remeck, Daniel G & Friedland, J.) (Marcel Dekker, Inc, NY, N.Y. 1997) (pgs. 427–443). These secreted factors can then cause local or systemic effects such as endotoxemia, intravascular coagulation and hypoxia. The oral feeding, thought to supply the offending microbe with a nutritional substrate, allows further intestinal colonization. Indeed, infant formula, which promotes malabsorption and is devoid of immunoprotective factors, is implicated in the pathogenesis of NEC. With a supply of substrate, events can progress rapidly, leading to death for a high percentage of infants with NEC.

There have been very few controlled studies of the various recommended treatment protocols for NEC. Since there is strong circumstantial evidence that NEC is initially caused by an infectious agent, antibiotics are used as a first line of defense. As soon as the disease is suspected, all enteral feeding is discontinued, and the infant is fed by parenteral alimentation. Parenteral broad-spectrum antibiotics such as carbenicillin or ticarcillin in combination with a second parenteral aminoglycoside such as gentamycin is then usually given. Ch. Fast and H. Rosegger, "Necrotizing enterocolitis prophylaxis, oral antibiotics and lyophilized entero-bacteria vs oral immunoglobulins" *Acta Paediatr Suppl* 396:86 (1994). Treatment periods typically last for 3 to 10 days. Drawbacks to these procedures, beyond the inability for them to work in 20–40% of the NEC cases are numerous. The aminoglycoside therapy requires monitoring if treatments are >3 days to avoid ototoxicity and nephrotoxicity. These broad-spectrum antibiotics can disrupt the establishment of the normal flora in the infant, important for proper nutrition and preventing opportunistic infections. A further potential danger is that the non-selectivity of antibiotics can promote widespread drug resistance in intestinal organisms, such as Enterococcus and Staphylococcus aureus whereas at present only one antibiotic is effective against them.

Apart from antibiotic use, another serious complication of the current treatment protocol is that removing the infant from enteral feedings can markedly influence gastrointestinal maturity. Enteral feedings stimulate a series of gut hormones such as motilin, gastrin and enteroglucagon which are important regulators of gastrointestinal function and mucosal growth. This increase of local "gut "hormones does not occur in infants fed with intravenous alimentation. Alterations of gut hormone physiology during prolonged periods of abstinence from enteric alimentation may place the immature intestine in jeopardy for mucosal atrophy, feeding intolerance and carbohydrate malabsorption. Accordingly, the sooner the patient receives enteral feedings the greater the chance of preventing the adverse effects of parenteral nutrition. At this point, a safer, more selective and effective therapeutic for NEC is desired.

Newer approaches to treat NEC have focused on prevention rather than treatment. Success thus far with newer approaches has been limited. Several studies have looked to determine if human breast milk feeding could possibly protect against the development of NEC. Human milk has many immunoprotective components such as lysozyme, PAF acetylhydrolase and immunoglobulin. Unfortunately, the studies have been inconclusive, and it appears that this approach does not decrease the severity and incidence of NEC. The use of human serum IgA-IgG administered orally to low-birth weight infants has been reported to have some benefit. M. M. Eibl et al., "Prevention of Necrotizing Enterocolitis in Low-Birth-Weight Infants by IgA-IgG Feeding" *New Eng. J Med.* 319:1 (1988). H. M. Wolf and M. M. Eibl, "The Relevance of Immunoglobulin in the Prevention of Necrotizing Enterocolitis," In: *Immunology of Milk and the Neonate* (Plenum Press, NY 1991). H. M. Wolf and M. M. Eibl, "The anti-inflammatory effect of an oral immunoglobulin (IgA-IgG) preparation and its possible relevance for the prevention of necrotizing enterocolitis," *Acta Paediatr Suppl.* 396:37 (1994).

Problems with these therapies may stem from the fact that the active ingredients or important antibody specificities in these treatments are unknown. This makes it very difficult to manufacture them consistently and reproducibly from preparation to preparation and achieve similar outcomes.

Recent studies have suggested that certain proinflammatory molecules including PAF, LPS and cytokines such as, TNF and IL-6 play an important role in the development of NEC in the newborn. Patients with NEC were reported to have higher levels of TNF, IL-1 and IL-6. D. Birk et al., "Is the elimination of endotoxin and cytokines with continuous lavage an alternative procedure in necrotizing enterocolitis?" *Acta Paediatr Suppl*. 396:24 (1994). Animal models for NEC indicate that the pathology associated with NEC can be generated by the administration of PAF, as well as various endotoxins and cytokines. W. Hsueh et al., "Platelet-activating factor: an endogenous mediator for bowel necrosis in endotoxemia," *FASEB J*. 1:403–405 (1987). X. Sun and W. Hsueh, "Bowel Necrosis Induced by Tumor Necrosis Factor in Rats Is Mediated by Platelet-activating Factor," *J. Clin. Invest.* 81:1328 (1988). Pretreatment of animals with a PAF antagonist, PAF-AH, has been shown to modify the development of NEC. M. Caplan et al., "The Role of Recombinant Platelet-Activating Factor Acetylhydrolase in a Neonatal Rat Model of Necrotizing Enterocolitis," *Ped. Research* 42:779 (1997). Interestingly, human milk has significant PAF-AH activity, whereas neonatal formulas have no measurable PAF-AH enzyme function. This difference may contribute to the lower incidence of NEC in breast milk-fed neonates.

Clearly there is a great need for agents capable of preventing and treating NEC. It would be desirable if such agents could be administered in a cost-effective and timely fashion, with a minimum of adverse side effects.

DEFINITIONS

The term "inflammatory mediator" refers to a variety of classes of molecules involved in an inflammatory response, including but not limited to proinflammatory phospholipids, chemokines [having both the C—C (e.g., Rantes, MIP-1α) and CXC (e.g., GRO-α, IP-10, etc.) motifs], adherence proteins (e.g., ICAM-1, selectin, VCAM, etc), leukotrienes, and cytokines (e.g., interleukins).

The phrase "symptoms of NEC" is herein defined to detected symptoms such as abdominal distension, gastrointestinal bleeding, and pneumatosis intestinalis. The phrase "wherein said symptoms are reduced" refers to a qualitative or quantitative reduction in detectable symptoms (e.g., reduced GI bleeding), including but not limited to a detectable impact on the rate of recovery from disease (e.g., rate of weight gain).

The phrase "at risk for NEC" is herein defined as encompassing the segment of the world population that has an increased risk for NEC. NEC is most commonly found in neonates, and in particular neonates in their first month of life and/or neonates with low birthweight (e.g., neonates weighing less than approximately 1,500 grams). Neonates with highest risk for NEC have been reported to be neonates weighing between approximately 750 and approximately 1,000 grams. T. L. Black et al., "Necrotizing Enterocolitis: Improving Survival Within a Single Facility," *S. Med. Journal* 82:1103 (1989).

The phrase "administered to or at the lumen" is herein defined as delivery to the space in the interior of the intestines. Such delivery can be achieved by a variety of routes (e.g., oral, rectal, etc.) in a variety of vehicles (e.g., tablet, suppository, etc.). In one embodiment, administration to or at the lumen results in delivery of antibody to the lamina propria (or regions of the intenstinal wall or radial to the mucosa). The lamina propria is classified as a loose, areolar, connective tissue but with lymphatic tendencies, the lymphoid material presumably functioning as a defense barrier against bacterial infection. When the antibody of the present invention is administered, the presence of the antibody in the intestinal wall can be readily detected by conventional means (e.g., staining and histology, labeled antibody and imaging, etc.).

SUMMARY OF THE INVENTION

The present invention relates to therapeutics for the prevention and treatment of necrotizing enterocolitis, and in particular the prevention and treatment of necrotizing enterocolitis in neonates through the use of antibody therapy. The examples of the present invention demonstrate a novel finding that antibodies against PAF or antibodies against TNF are effective (as demonstrated in an experimental model of NEC) in preventing NEC.

It is not intended that the present invention be limited to a particular type of antibody. Polyclonal and monoclonal antibodies are contemplated in the context of the present invention. Such antibodies may be made in a variety of animals [e.g., rabbits, horses, cows (e.g., in the milk), and birds]. The present invention also contemplates human and "humanized" antibodies.

It is preferred that the antibodies not be complement fixing. More specifically, avian antibodies (e.g., chicken antibodies from eggs) are preferred. It is contemplated that the treatment with such antibodies will have the desired result of reducing mortality rates caused by NEC.

In one embodiment, the present invention contemplates a method comprising the administration of antibodies which bind to inflammatory mediators such as PAF or TNF. Preferably, the antibody is reactive with PAF or TNF across species. Specifically, the present invention demonstrates that immunization with human TNF generates neutralizing antibody capable of reacting with endogenous murine TNF. Thus, the present invention provides anti-TNF antibody that will react with mammalian TNF generally. In another embodiment, the antibodies are combined with other reagents (including but not limited to other antibodies).

In another embodiment, the present invention contemplates a method of treating neonates at risk for NEC. For example, the present invention contemplates a method of treatment, comprising: (a) providing: i) a neonate at risk for necrotizing enterocolitis; ii) a therapeutic preparation, comprising anti-PAF antibodies and (b) administering said antibodies to said neonate (e.g., administering to the intestinal lumen of said neonate). In another embodiment, the present invention contemplates a method of treatment, comprising: (a) providing: i) a neonate at risk for necrotizing enterocolitis; ii) a therapeutic preparation, comprising anti-TNF antibodies and (b) administering said antibodies to said neonate (e.g., administering to the intestinal lumen of said neonate).

The present invention also contemplates a method for reducing the symptoms of NEC. In one embodiment, the present invention contemplates a method of treatment, comprising: (a) providing: i) a neonate with symptoms of necrotizing enterocolitis; ii) a therapeutic preparation, comprising anti-PAF antibodies and (b) administering said antibodies to said neonate (e.g., administering to the intestinal lumen of said neonate) under conditions wherein at least one of said symptoms is reduced. In another embodiment, the present invention contemplates a method of treatment, comprising: (a) providing: i) a neonate with symptoms of necrotizing enterocolitis; ii) a therapeutic preparation, comprising anti-TNF antibodies and (b) administering said antibodies to said neonate (e.g., administering to the intestinal lumen of said neonate) under conditions wherein at least one of said symptoms is reduced.

DESCRIPTION OF THE INVENTION

The present invention relates to therapeutics for the prevention and treatment of necrotizing enterocolitis, and in particular the prevention and treatment of necrotizing enterocolitis in neonates through the use of avian polyclonal antibody therapy. More specifically, the present invention contemplates prevention and treatment of necrotizing enterocolitis in neonates through the administration (e.g., oral administration) of antibodies to cytokines and other inflammatory mediators.

It is not intended that the present invention be limited to a particular mediator. A variety of these mediators can be used to generate antibodies useful in the prevention and treatment of necrotizing enterocolitis. Illustrative inflammatory mediators are set forth in Table 1.

While not limited to particular inflammatory mediator, the preferred antibodies are directed to PAF and/or TNF. The present invention contemplates treatments

TABLE 1

| Name | Abbr. | Type | Specific Name |
|---|---|---|---|
| Interferons | IFN | alpha | Leukocyte Interferon |
|  |  | beta | Fibroblast Interferon |
|  |  | gamma | Macrophage Activation Factor |
| Interleukins | IL-1 | 1 alpha | Endogenous Pyrogen |
|  |  | 1 beta | Lymphocyte-Activating Factor |
|  |  | 1 ra | IL-1 Receptor Antagonist |
|  | IL-2 |  | T-cell Growth Factor |
|  | IL-3 |  | Mast Cell Growth Factor |
|  | IL-6 |  | Hybridoma Growth Factor |
|  | IL-7 |  | Lymphopoietin |
|  | IL-8 |  | Granulocyte Chemotactic Protein |
|  | IL-9 |  | Megakaryoblast Growth Factor |
|  | IL-11 |  | Stromal Cell-Derived Cytokine |
|  | IL-12 |  | Natural Killer Cell Stimulatory Factor |
|  | IL-15 |  | T-cell Growth Factor |
| Tumor Necrosis Factors | TNF | alpha | Cachectin |
|  |  | beta | Lympbotoxin |
| Colony Stimulating Factors | CSF | GM-CSF | Granulocyte-macrophage Colony-Stimulating Factor |
|  |  | Mp-CSF | Macrophage Growth Factor |
|  |  | G-CSF | Granulocyte Colony-stimulating Factor |
|  |  | EPO | Erythropoietin |
| Transforming Growth Factor | TGF | beta 1 | Cartilage-inducing Factor |
|  |  | beta 2 | Epstein-Barr Virus-inducing Factor |
|  |  | beta 3 | Tissue-derived Growth Factor |
| Other Growth Factors | LIF |  | Leukemia Inhibitory Factor |
|  | MIF |  | Macrophage Migration-inhibiting Factor |
|  | MCP-1 |  | Monocyte Chemoattractant Proteins |
|  | MCP-2 |  |  |
|  | MCP-3 |  |  |
|  | EGF |  | Epidermal Growth Factor |
|  | PDGF |  | Platelet-derived Growth Factor |
|  | FGF | alpha | Acidic Fibroblast Growth Factor |
|  |  | beta | Basic Fibroblast Growth Factor |
|  | ILGF |  | Insulin-like Growth Factor |
|  | NGF |  | Nerve Growth Factor |
|  | BCGF |  | B-cell growth factor | comprising anti-PAF antibodies and/or anti-TNF antibodies prior to and after onset of symptoms of NEC. In accordance with the present invention, antibody formulations are administered via intravenous, parenteral, rectal or oral route, although the present invention is not limited to these methods of administration. The antibodies can be used alone (e.g., anti-PAF alone) or in combination (e.g., anti-PAF together with anti-TNF—or another antibody to one of the above-described mediators).

It is not intended that the present invention be limited by the particular nature of a formulation or combination. The present invention contemplates combinations as simple mixtures as well as chemical hybrids. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as sprays (e.g., intranasal aerosols) for topical use. However, they may also be prepared either as liquid solutions or suspensions, or in solid forms. Oral formulations (e.g., for gastrointestinal inflammation) usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antibodies of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

It is preferred that the antibodies of the present invention be treated to inactivate pathogens (e.g., bacteria and viruses) prior to administration. A variety of approaches can be used including psoralens, solvent/detergent, and heat.

Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light (UVA). G. D. Cimino et al., Ann. Rev. Biochem. 54:1151 (1985); and Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., *Biochemistry* 16:1058 (1977); J. Tessman et al., *Biochem.* 24:1669 (1985); and Hearst et al., U.S. Pat. Nos. 4,124,589, 4,169,204, and 4,196,281, hereby incorporated by reference. Psoralens have been shown to inactivate viruses in some blood products. See H. J. Alter et al., *The Lancet* (ii:1446) (1988); L. Lin et al., *Blood* 74:517 (1989); and G. P. Wiesehahn et al., U.S. Pat. Nos. 4,727,027 and 4,748,120, hereby incorporated by reference.

The solvent/detergent approach involves the treatment of antibody or antibody-containing serum or plasma with solvents and/or detergents. See B Horowitz et al., *Transfusion* 25:516 (1985). The process is believed to work by solubilization of the pathogen membrane.

Heat treatment can also be used. See J. Hilfenhous et al., *J Biol. Std*. 70:589 (1987). Typically, useful temperatures are those that are less than 70° C. Heat treatment can be done on antibody-containing serum or plasma. Alternatively, heat treatment can be performed on partially purified or purified antibody. In the case of antibodies from eggs, antibody is perferably isolated by extraction (e.g., with water or PEG) and precipitation (e.g., ammonium sulfate). After filtration or dialysis, the purified egg antibody can be heat treated. Sugars (e.g., sucrose) or inert proteins can be added to the antibody to stabilize the antibody during the heat treatment. The heat treated material can thereafter, if desired, be treated with further filtration or dialysis.

EXPERIMENTAL

The following examples serve to illustrate certain preferred embodiments and aspects of the present invention and are not to be construed as limiting the scope thereof.

EXAMPLE 1

Production of Antibodies to TNF in the Hen

This example involved (a) preparation of the immunogen and immunization, (b) purification of anti-TNF chicken antibodies from egg yolk (IgY), and (c) detection of anti-TNF antibodies in the purified IgY preparations.

(a) Preparation of the immunogen and immunization. Recombinant human Tumor Necrosis Factor Alpha, (TNF) was purchased (lyophilized without bovine serum albumin (BSA) and designated carrier-free) from R&D Systems Inc., Minneapolis, Minn. and produced in *E. coli*. The lyophilized TNF was reconstituted in phosphate-buffered saline pH 7.2–7.5 (PBS) at 50 $\mu$g/ml and from 2–10 $\mu$g of TNF was used to immunize each hen. Each hen received one 0.5 ml sub-cutaneous injection containing TNF with 75 $\mu$g Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4–6 weeks.

(b) Purification of anti-TNF chicken antibodies from egg yolk (IgY). Groups of eggs were collected per immunization group at least 3–5 days after the last booster immunization. The chicken yolk immunoglobulin (IgY) was extracted by a two-step polyethylene glycol (PEG) 8000 method performed according to a modification of the procedure of Polson et al., *Immunol. Comm.*, 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes. The supernatants were decanted and filtered through 4 layers of gauze to remove the floating particulates and a second PEG step was performed by adding PEG to a final concentration of 12% (the supernatants were assumed to contain 3.5% PEG). After a second centrifugation, the supernatants were discarded and the IgY pellets were resuspended in 0.1M carbonate buffer (pH 9.5) at approximately ⅙ the original yolk volume. IgYs extracted from the eggs of immunized hens are designated as "immune IgY," while IgYs extracted from the eggs of unimmunized hens is designated "preimmune IgY." The concentration of the fractionated IgY's were estimated by measuring the absorbance at 280 nm (an optical density at 280 nm of 1.3 equals 1 mg of IgY/ml. The antibody concentrations were about 25–30 mg/ml.

(c) Detection of anti-TNF antibodies in the purified IgY preparations. In order to determine if anti-TNF response was generated and to determine relative levels of the response, enzyme-linked immunosorbent assays (ELISA) were performed. Briefly, ninety-six well Falcon Pro-bind micro-titer plates were coated overnight at 4° C. with 100 $\mu$l/well of TNF at 0.1–1.0 $\mu$g/ml PBS. The wells are then blocked with PBS containing 1% BSA and 0.05% Tween 20 and incubated for about 1 hour at 37° C. The blocking solution was removed and the immune or preimmune IgY was diluted in PBS containing BSA and the plates were incubated for 1 hour at 37° C. The plates were washed 3 times with PBS containing 0.05% Tween 20 and three times with PBS alone. Alkaline phosphatase-conjugated anti-chicken IgG was diluted 1:1000 in PBS containing 1% BSA and 0.05% Tween 20, added to the plates and incubated 1 hour at 37° C. The plates were washed as above and p-nitrophenyl phosphate at 1 mg/ml in 0.05 M $Na_2CO_3$, pH 9.5, 10 mM $MgCl_2$ was added. The plates were read in a Dynatech plate reader at 410 nm about 30 minutes after substrate addition. Good antibody titers (reciprocal of the highest immune IgY generating a signal about 3-fold higher than that of preimmune) ranging from 10,000 to 50,000 was generated.

The level of antibody response in the hens against TNF, given the low amounts of antigen used for immunization, indicates that this protein is very immunogenic in the hens and is a well-suited system to generate anti-mammalian TNF antibodies.

EXAMPLE 2

Production of Antibodies to PAF in the Hen

This example involved (a) preparation of the immunogen and immunization, (b) purification of anti-PAF chicken antibodies from egg yolk (IgY), and (c) detection of anti-PAF antibodies in the purified IgY preparations.

(a) Preparation of the immunogen and immunization. The phospholipid L-α-phosphatidylcoline B-acetyl-α-o-alkyl (PAF) was purchased (lyophilized)from Sigtma (St. Louis, Mo.). The lyophilized PAF was reconstituted in ethanol (5 mg/ml) and between 200 and 250 ug were used per hen to immunize.

Each hen received one 0.5 ml sub-cutaneous injection containing PAF with 75 $\mu$g Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4–6 weeks.

(b) Purification of anti-PAF chicken antibodies from egg yolk (IgY). Groups of eggs were collected per immunization group at least 3–5 days after the last booster immunization. The chicken yolk immunoglobulin (IgY) was extracted by a two-step polyethylene glycol (PEG) 8000 method performed according to a modification of the procedure of Polson et al., *Immunol. Comm.*, 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes. The supernatants were decanted and filtered through 4 layers of gauze to remove the floating particulates and a second PEG step was performed by adding PEG to a final concentration of 12% (the supernatants were assumed to contain 3.5% PEG). After a second centrifugation, the supernatants were discarded and the IgY pellets were resuspended in 0.1M carbonate buffer (pH 9.6) at approximately ⅙ the original yolk volume. IgYs extracted from the eggs of immunized hens are designated as "immune IgY," while IgYs extracted from the eggs of unimmunized hens is designated "preimmune IgY." The concentration of the fractionated IgY's were estimated by measuring the absorbance at 280 nm (an optical density at 280 nm of 1.3 equals 1 mg of IgY/ml. The antibody concentrations were about 25–30 mg/ml.

(c) Detection of anti-PAF antibodies in the purified IgY preparations. In order to determine if anti-PAF response was generated and to determine relative levels of the response, enzyme-linked immunosorbent assays (ELISA) were performed. Briefly, ninety-six well Falcon Pro-bind micro-titer plates were coated overnight at 4° C. with 100 μl/well of PAF at 2–10 μg/ml PBS. The wells are then blocked with PBS containing 1% Gelatin and incubated for about 1 hour at 37° C. The blocking solution was removed and the immune or preimmune IgY was diluted in PBS containing 0.1% Gelatin and 0.1% Tween 20, and the plates were incubated for 1 hour at room temperature (RT). The plates were washed 3 times with PBS containing 0.1% Tween 20. Alkaline phosphatase-conjugated anti-chicken IgG was diluted 1:1000 in PBS containing 0.1% Gelatin and 0.1% Tween 20, added to the plates and incubated ½ hour at RT. The plates were washed as above and Blu-Phos™ alkaline phosphatase (KPL, Gaithersburg, Md.) was added. The plates were read in a Dynatech plate reader at 610 nm about 15–30 minutes after substrate addition. Antibody titers (reciprocal of the highest immune IgY generating a signal about 3-fold higher than that of preimmune) were found to be about 250.

The antibody response in the hens against PAF indicates that this phospholipid is immunogenic in the hens and is a well-suited system to generate anti-PAF antibodies.

EXAMPLE 3

Anti-TNF Cell Neutralization Assay

This example demonstrates the neutralization capabilities of the anti-TNF IgY antibodies in an in vitro cell based bioassay. The cytolytic effect of TNF on the murine cell line L929 (ATCC CCL 1) in the presence of actinomycin D was previously described by Mathew, N. et al., (1987) Lymphokines and Interferons, a practical approach. M. J. Clemens, A. G. Morris and A. J. H Gearing , eds. IRL. Press. P.221. In the presence of neutralizing anti-TNF, TNF mediated cell death in the L929 cells should be prevented. L929 cells were grown in sterile conditions with Ham's F12 and Dulbecco's modified Eagle's media (1:1 vol:vol ratio) (Life Technologies) containing 1.2 g/l sodium bicarbonate, 15 mM HEPES (Life Technologies), and supplemented with 10% vol:vol bovine serum (Life Technologies). Cells were harvested using trypsin:EDTA (Life Technologies) and $2 \times 10^4$ cells were dispensed into the wells of a 96-well plate (Corning) and incubated 24 hours at 37(C., 5% $CO_2$, in a humidified atmosphere. Anti-TNF IgY and preimmune IgY, were serially diluted and added to recombinant human TNF at 1.0 ng/ml (R&D Systems, MN) with 10 μg/ml actinomycin D (ICN Biomedicals, Inc., Ohio) for 1 hour. After addition to the cells, the final concentrations of antibodies, TNF, and actinomycin D in each well were 1.0–0.002 μg/ml, 0.05 ng/ml, and 1.0 μg/ml respectively. After approximately 20 hours, cell death was measured using Cell Titre96 Cell Proliferation Assay (Promega Corporation) by adding 15 μl/well of the dye solution and measuring the OD at 490 nm. See Table 2 below.

TABLE 2

| Antibody Concentration (μg/ml) | Percent Neutralization Anti-TNF IgY |
| --- | --- |
| 1.0 | 94 (+/−) 12% |
| 0.5 | 96 (+/−) 10% |
| 0.25 | 85 (+/−) 7% |
| 0.12 | 87 (+/−) 3% |
| 0.062 | 90 (+/−) 16% |
| 0.031 | 85 (+/−) 7% |
| 0.016 | 33 (+/−) 8% |
| 0.008 | 18 (+/−) 10% |
| 0.004 | 13 (+/−) 9% |
| 0.002 | 6 (+/−) 3% |

As is seen in the table above, the amount of anti-TNF which resulted in prevention of cell death in 50% of the cells was measured at 20 ng/ml. There was no measurable neutralization of the TNF at any concentration (1.0 μg/ml–0.002 μg/ml) using the preimmune IgY. These results indicate that avian anti-TNF is quite effective at neutralizing the effects of TNF in this cell-based assay.

EXAMPLE 4

Agglutination Assay Using Anti-PAF

This example demonstrates the specificity of the anti-PAF antibodies for the PAF antigen using an agglutination assay. Agglutination of PAF antigen by anti-PAF antibodies is performed as described by J. Nishihira, et al. (J.Biochem. 95:1247–1251 (1984)). The PAF antigen (L-alpha-phoshatidylcholine, beta-acetyl-gamma-O-alkyl) (Sigma) was combined with phosphatidylcholine (Sigma) and cholesterol (Sigma) in a ratio of 0.03:0.3:0.9 μg of each/ml and vortexed for several minutes. To an agglutination plate, 10 μl of antigenic mixture was added to either anti-PAF IgY or preimmune IgY (30 mg/ml). Presence of precipitate in the well was only seen in the anti-PAF/PAF mixture; there was no apparent precipitation in the preimmune/PAF control mixture. Agglutination was observed microscopically at 40-fold magnification as a precipitate in the well. In the well containing preimmune IgY, there was no apparent agglutination upon the addition of the antigenic mixture, as confirmed by microscopic evaluation at 40-fold magnification. In addition to the ELISA assay in Example 3(c), these results confirm the specificity of the anti-PAF IgY for the PAF antigen.

EXAMPLE 5

Animal Model of Bowel Necrosis

In order to determine whether anti-TNF or anti-PAF polyclonal antibodies are capable of neutralizing the effects of bowel necrosis in vivo, a rodent model of necrotizing enterocolitis was utilized. This model uses PAF to simulate intestinal necrosis which is characterized by the gross and histological pathological features similar to those found in adult patients with ischemic bowel disease or in neonates with NEC. (See F. Gonzalez-Cruzzi and W. Hsueh, Am J Pathol, 112:127–135 (1993)). To induce bowel necrosis, rats are systemically treated with a low dose (1–3 ug) of PAF which reproducibly results in severe bowel necrosis within 2 hours. This example involves a dose response study with PAF to determine the optimal dose of PAF that exhibits symptoms of bowel necrosis.

Acute bowel necrosis by PAF was induced in Sprague Dawley rats (200–225 g), (Charles River) essentially as described by F. Gonzalas-Cruzzi and W. Hsueh (1993). The appropriate amount of PAF necessary to induce bowel injury in rats was first necessary to be determined, but has been reported to be in the range of about 3 ug/kg (See W. Hsueh et al. Interaction of Inflammatory Cytokines, Bacterial Products, and Lipid Mediators in Intestinal Injury; In Cytokines in Health and Disease). Rats were sedated before PAF injection using ether or using a xylazine/ketamine/water mixture. For the ether sedation, rats were sedated for several minutes after being placed in a jar with ether soaked gauze. Using ether, the rats remained sedated for only several minutes. For the xylazine/ketamine/water sedative, stock solutions in sterile water (Baxter) of xylazine (Sigma) at 20 mg/ml and ketamine (Sigma) at 100 mg/ml were mixed at a working solution of 1:1:5 of xylazine, ketamine and sterile water. Rats received 3 mls/kg or about 0.6 mls per rat intraperitoneally (i.p.) using a 27 G, 1 ml syringe. At this concentration the rats remained sedated for about 1 hour. Stock PAF (L-alpha-phosphatidylcholine, beta-acetyl-gamma-O-alkyl) (Sigma), was prepared by resuspending the dry material in 0.01% bovine serum albumin in sterile saline at a concentration of 2 mg/ml. The stock solution was diluted in sterile saline (Baxter) at various concentrations of 0.3, 0.6, 1.2, and 2.4 micrograms of PAF per 100 microliters of saline. After xylazine/ketamine sedation, rats were injected via the tail vein using a 1 ml syringe with a 27 G needle with 100 microliters of the different doses of PAF. Immediately after PAF administration, the rats in all the dose groups began to display very labored breathing. Within 15 to 20 minutes after PAF challenge, the rats given the higher doses of PAF of 1.2 and 2.4 ug died. These rats upon necropsy displayed the gross morphological changes of the small bowel that is typical of PAF induced toxicity. Blood vessels in the large and small bowel were dilated and inflamed. Large sections of the small bowel contained large amounts of blood in the lumen with areas of necrosis. Two hours after PAF challenge rats given the lower doses of PAF were sacrificed and inspected for gross organ pathology. The animal given 0.6 ug of PAF showed similar organ pathology as the higher doses but to a lesser extent. The areas of congestion, redness and inflammation was more patchy throughout the small bowel. In contrast, the organ pathology of the rat with the lowest dose of PAF showed normal or near normal gross appearance.

Experiments were also performed in rats sedated with ether and challenged with 1.2 ug of PAF. While rats sedated with ether normally revive within minutes, the ether sedated rats given PAF remained sedated for 1 hour or more. In addition, the PAF effects were found to be slightly less adverse in terms of mortality than that found using the xylazine/ketamine sedation. Less animals died from the PAF treatment, when sedated with ether, although the gross organ pathology between the two sedation methods at the same PAF dose were largely the same. This difference may be due to the synergistic depressive side effects of the xylazine/ketamine with PAF has on basal respiration and heart rate in the rats.

The results of these experiments using both sedation methods demonstrated a dose response in rats to PAF and that PAF doses of 1.2 ug or more were found to optimally mimic the same effects reported to be seen in ischemic bowel necrosis and NEC. A sub-lethal dose of 1.2 ug for rats at 200–225 grams were used in subsequent in vivo treatment studies.

EXAMPLE 6

Prevention of Acute Bowel Necrosis in Vivo by the Administration of Avian Polyclonal Anti-TNF or Anti-PAF The rat model described in Example 5 was used to determine whether the avian anti-TNF or anti-PAF is effective at preventing lethality and bowel necrosis induced by PAF. Rats were pretreated either parenterally (i.p.) or orally with antibodies before an i.v. PAF challenge (1.2 ug of PAF/rat). The mortality and morbidity in the rats were then assessed in the different treatment groups 2 hours post-PAF challenge. This example involves: (a) Pretreatment studies were the anti-TNF or anti-PAF is administered parenterally before PAF challenge. (b) Pretreatment studies were the anti-TNF or anti-PAF is administered orally before PAF challenge (a) Several experiments were conducted to determine if the adverse effects induced by PAF in the rats could be prevented using either avian anti-TNF or anti-PAF when administered parenterally. Treatment groups consisted of rats treated with: a) vehicle (0.1 M carbonate pH 9.5); b) preimmune IgY; c) anti-TNF; and d) anti-PAF. In some experiments, normal rats were not treated with PAF and were either untreated (Normal control) or pretreated i.p. with IgY(Treated controls) and served as negative controls. The Treated controls were run to rule out the possibility that antibodies alone would cause small bowel pathology in the rats. One or two, 1 ml doses of vehicle or IgY treatments containing approximately 30 mg/ml of IgY in carbonate buffer pH 9.5 were administered up to 1 hour before PAF challenge. The rats were lightly sedated with ether before treatment and the antibodies or vehicle was administered i.p. using 1 ml syringe using a 27 G needle. Rats were then challenged after light ether sedation with an i.v. injection (27 G needle) in the tail vein with 100 ul of saline containing 1.2 ug of PAF. For the PAF administration, rats were placed in a restrainer and the tail vein was dilated by placing the tail in warm water to make the veins more visible for injection. Two hours after PAF challenge, the surviving animals were sacrificed and the gross appearance of the small bowel was semi-quantitated using a morbidity scoring system. Animals that died from PAF toxicity before the two hour time point were immediately necropsied and small bowel morbidity was also scored. The ability of anti-TNF or anti-PAF to prevent mortality and small bowel pathology (morbidity) in the rats is shown in Table 3. The cumulative mortality indicates the percentage of the rats that died from PAF toxicity. The small bowel morbidity score of 0–4 reflected the gross appearance of the small bowel. The scoring was as follows: a score of 0 for normal, 1+ for mild congestion with some luminal mucus, 2+ for moderate congestion with rare gross necrosis, 3+ for moderate congestion with necrosis and blood in the lumen, 4+ for severe congestion and necrosis with large amounts of blood in the lumen.

No pathology was seen in the treated controls rats (without PAF challenge) after i.p. treatment with IgY and the small bowel gross appearance was identical to that of the normal controls. PAF challenge of the vehicle and Preimmune-treated rats resulted in some mortality and extensive small bowel morbidity with a very high morbidity score of about 3.5 out of a maximum of 4. In contrast, both groups of PAF treated rats that were i.p. pretreated either with anti-TNF or anti-PAF showed a marked reduction of small bowel morbidity with no mortality from PAF toxicity. These results indicate that the parenteral pretreatment of either anti-TNF or anti-PAF is effective at preventing bowel necrosis in this model *(p value<0.05 for both anti-TNF and anti-PAF morbidity scores as compared to vehicle or pre-immune controls).

TABLE 3

| Treatment Group | No. Of Expts. | No. Of Animals | % Cumulative Mortality | Cumulative Morbidity Score |
|---|---|---|---|---|
| 1) Normal control | 1 | 1 | 0 | 0 |
| 2) Treated controls | 1 | 4 | 0 | 0 |
| 3) Vehicle | 4 | 6 | 33 | 3.5 |
| 4) Preimmune | 5 | 10 | 10 | 3.6 |
| 5) Anti-TNF | 5 | 10 | 0 | 1.5* |
| 6) Anti-PAF | 5 | 11 | 0 | 1.3* |

In addition to the % morbidity and the scoring of gross pathology of the small bowels in the rats, histological evaluation of specimens were evaluated and the level of pathology was quantitated. A 5–6 cm segment of small bowel from the same region in each rat from the different treatment groups were removed and processed for sectioning and Hemoxylin and Eosin (H&E) staining. The segment of small bowel was cut longitudinally, pinned lumen side-up to a piece of styrofoam. The specimens were then fixed by floating the pinned lumen-side down in 10% formalin in phosphate-buffered saline pH 7.2. for at least 18 hours. The specimens were then fixed, embedded in paraffin, sectioned to slides and stained with H&E stain for histological examination. The small bowel samples were sectioned by placing the specimen on its edge and cutting sections parallel to the long axis of the specimen. This sectioning procedure enabled one to evaluate large area of small bowel per section and visualize the full-depth of the villi and associated structures of the small intestine. After microscopic evaluation the degree of pathology present was scored using a histological scoring method described by Michael Caplan, et al., Ped. Res., 42:6, 779–783 (1997). Briefly, a score of 1+was assigned to sections that are normal in appearance, or with mild epithelial cell lifting or separation, 2+ for necrosis down to the mid-villous level, 3+ for the necrosis of the entire villi, and 4+ for transmural necrosis. The histology scores of the small intestines are shown in the Table 4 as the mean +/− SEM of each treatment group. The Mann-Whitney test was used to determine the statistical difference between treatment groups, and a p value less than 0.05 was considered significant.

TABLE 4

| Treatment Group | No. Of Expts. | No. of Animals | Mean +/− SEM Of Histology Score |
|---|---|---|---|
| 1) Normal control | 1 | 1 | 1.0 (+/−) 0.0 |
| 2) Treated control | 1 | 4 | 1.0 (+/−) 0.0 |
| 3) Pre-immune | 2 | 7 | 2.3 (+/−) 0.5 |

TABLE 4-continued

| Treatment Group | No. Of Expts. | No. of Animals | Mean +/− SEM Of Histology Score |
|---|---|---|---|
| 4) Anti-TNF | 1 | 5 | 2.1 (+/−) 0.2 |
| 5) Anti-PAF | 2 | 7 | 1.6 (+/−) 0.5* |

As seen in the table, the anti-PAF delivered intraperitoneally, significantly reduced the microscopic histological damage as compared to the preimmune treated controls (p value<0.05). However, the anti-TNF had only a slightly protective effect as compared to the preimmune control (p value>0.05). These results indicate that the anti-PAF antibodies are effective in preventing the tissue injury that normally results from PAF associated bowel necrosis.

(b) In addition to the parenteral pretreatment studies, experiments were conducted to determine if PAF induced bowel necrosis in the rats can be prevented using either avian anti-TNF or anti-PAF when administered orally. Treatment groups consisted of rats treated with: a) vehicle (0.1 M carbonate pH 9.5); b) preimmune IgY; c) anti-TNF; and d) anti-PAF. As described in Example 6 (a), some normal rats were not treated with PAF and were either untreated (Normal control) or pretreated orally with IgY(Treated controls) and served as negative controls. Two mls of either vehicle or IgY containing approximately 30 mg/ml of IgY in carbonate buffer pH 9.5 were administered 1 hour and again approximately 15 minutes before PAF challenge. Before treatment, rats were lightly sedated with ether and then treated orally using a 5 ml syringe using a 5 cm 18 G feeding needle (Popper and Sons). Rats were then challenged with an i.v. injection (27 G needle) in the tail vein with 100 ul of saline containing 1.2 ug of PAF as described above. The ability of orally administered anti-TNF or anti-PAF to prevent mortality and small bowel pathology (morbidity) in the rats two hours after PAF treatment was assessed as described above in (a). The mortality and gross morbidity results in the rats after oral IgY treatments is shown in Table 5.

TABLE 5

| Treatment Group | No. Of Expts. | No. Of Animals | % Cumulative Mortality | Cumulative Morbidity Score# |
|---|---|---|---|---|
| 1) Normal coutrol | 1 | 1 | 0 | 0 |
| 2) Treated control | 1 | 3 | 0 | 0 |
| 3) Vehicle | 1 | 3 | 0 | 4.0 |
| 4) Preimmune | 4 | 11 | 45 | 3.4 |
| 5) Anti-TNF | 2 | 6 | 0 | 0.8* |
| 6) Anti-PAF | 3 | 10 | 0 | 0.6* |

As seen in Table 5, no pathology was seen in the treated controls rats (without PAF challenge) after oral treatment with IgY and the small bowel gross appearance was identical to that of the normal controls. Groups orally pretreated either with anti-TNF or anti-PAF were effectively treated against PAF toxicity. Both groups showed a significant reduction in small bowel morbidity with no mortality from PAF toxicity. Morbidity scores in the anti-TNF and anti-PAF treated groups had statistically significant lower average morbidity score of about 0.7, as compared to a score of 4.0 and 3.4 for vehicle-treated and Preimmune-treated rats *(p value<0.05 for both treatment groups). Overall, mortality in the preimmune-treated rats was very high. In contrast, both these results indicate that the oral pretreatment of either anti-TNF or anti-PAF is effective at preventing bowel necrosis in this model. These results also support the experiments where the parenteral pretreatment of anti-TNF or anti-PAF could effectively prevent bowel necrosis by PAF. The histological evaluation of specimens after sectioning and H&E staining were evaluated and the level of pathology was quantitated. The histology slides of the small bowel specimens were processed and scored as described above in Example 6 (a). The results from data from several combined experiments are shown in Table 6.

TABLE 6

| Treatment Group | No. Of Expts. | No. Of Animals | Mean +/− SEM Of Histology Score |
|---|---|---|---|
| 1) Normal control | 1 | 1 | 1.0 (+/−) 0.0 |
| 2) Treated control | 1 | 3 | 1.0 (+/−) 0.0 |
| 2) Vehicle | 1 | 3 | 2.3 (+/−) 0.6 |
| 3) Pre-immune | 3 | 10 | 3.4 (+/−) 0.5 |
| 4) Anti-TNF | 1 | 5 | 1.4 (+/−) 0.6* |
| 5) Anti-PAF | 3 | 10 | 1.3 (+/−) 0.5* |

As seen in table 5, the animals treated orally with anti-TNF and anti-PAF had significantly less histological damage as compared to the preimmune treated controls (p value<0.001). In fact, the histological scores for the anti-TNF and anti-PAF antibody treated animals approached the values seen for the normal control group. These results indicate the potent ability of these antibodies, delivered orally, to protect the small bowel from the toxic effect of PAF.

Those skilled in the art will know, or be able to ascertain upon review of the above, using no more than routine experimentation, many equivalents to the specific embodiments of the invention described herein. These and all other equivalents are intended to be encompassed by the following claims.

What is claimed is:

1. A method of treatment, for necrotizing enterocolitis comprising:

a) providing:

i) a human neonate, wherein said human neonate has symptoms of necrotizing enterocolitis, ii) a therapeutic formulation comprising avian polyclonal antibody directed to platelet activating factor, and;

b) administering said formulation to said human neonate.

2. The method of claim 1, wherein said human neonate is a low birth weight neonate.

3. The method of claim 1, wherein said administering is performed orally.

4. The method of claim 1, wherein said administering is performed parenterally.

5. The method of claim 1, wherein said administering is performed rectally.

6. A method of treatment, for necrotizing enterocolitis comprising:

a) providing:

i) a human neonate at risk for necrotizing enterocolitis, ii) a therapeutic formulation comprising avian polyclonal antibody directed to platelet activating factor, and;

b) administering said formulation to the lumen of the intestine of said neonate.

7. The method of claim 6, wherein said human neonate is a low birth weight neonate.

8. The method of claim 6, wherein said administering is performed orally.

9. The method of claim 6, wherein said administering is performed parenterally.

10. The method of claim 6, wherein said administering is performed rectally.

* * * * *